US009982012B2

(12) United States Patent
Parayitam et al.

(10) Patent No.: US 9,982,012 B2
(45) Date of Patent: May 29, 2018

(54) REFOLDING OF GRANULOCYTE COLONY STIMULATING FACTOR

(71) Applicant: DR. REDDY'S LABORATORIES, Hyderabad (IN)

(72) Inventors: Bharata Ratnam Parayitam, Mahabubnagar (IN); Ravikant Devakate, Nanded (IN); Neeraj Narayanan, Calicut (IN); Gopinath Govindarajan, Chennai (IN); Vivek Arthanari, Salem (IN); Jaby Jacob, Hyderabad (IN)

(73) Assignee: DR. REDDY'S LABORATORIES LIMITED, Hyderabad (IN)

( * ) Notice: Subject to any disclaimer, the term of this patent is extended or adjusted under 35 U.S.C. 154(b) by 38 days.

(21) Appl. No.: 14/779,485

(22) PCT Filed: Mar. 28, 2014

(86) PCT No.: PCT/IB2014/060251
§ 371 (c)(1),
(2) Date: Sep. 23, 2015

(87) PCT Pub. No.: WO2014/155349
PCT Pub. Date: Oct. 2, 2014

(65) Prior Publication Data
US 2016/0031932 A1 Feb. 4, 2016

(30) Foreign Application Priority Data
Mar. 29, 2013 (IN) .......................... 1431/CHE/2013

(51) Int. Cl.
*C07K 1/113* (2006.01)
*A61K 38/19* (2006.01)
*C07K 14/535* (2006.01)

(52) U.S. Cl.
CPC .......... *C07K 1/1136* (2013.01); *A61K 38/193* (2013.01); *C07K 14/535* (2013.01)

(58) Field of Classification Search
CPC ... C07K 1/1136; C07K 14/535; A61K 38/193
See application file for complete search history.

(56) References Cited

U.S. PATENT DOCUMENTS

| 5,849,883 A | 12/1998 | Boone et al. |
| 7,538,198 B2 | 5/2009 | Randolph et al. |
| 8,703,123 B2 | 4/2014 | Hinderer et al. |
| 2001/0044521 A1 | 11/2001 | Lin |
| 2003/0166062 A1 | 9/2003 | Gonzalez-Villasenor |
| 2011/0034678 A1 | 2/2011 | Froland et al. |
| 2011/0294990 A1 | 12/2011 | Pizarro et al. |
| 2012/0093765 A1 | 4/2012 | Somani et al. |

FOREIGN PATENT DOCUMENTS

| EP | 0547102 B1 | 6/1993 |
| EP | 1449848 A1 | 8/2004 |
| EP | 1630173 B1 | 11/2009 |
| WO | 2008/096370 A2 | 8/2008 |
| WO | WO2010/146599 | * 12/2010 |

OTHER PUBLICATIONS

International Search Report dated Jan. 6, 2015, for corresponding International Patent Application No. PCT/IB2014/060251.
Written Opinion dated Jan. 6, 2015, for corresponding International Patent Application No. PCT/IB2014/060251.
International Preliminary Report on Patentability dated Sep. 29, 2015, for corresponding International Patent Application No. PCT/IB2014/060251.
Reubsaet et al., "Oxidation of recombinant methionyl human granulocyte colony stimulating factor", Journal of Pharmaceutical and Biomedical Analysis, 1998, pp. 283 to 289, vol. 17, Elsevier Science B.V.
Extended European Search Report dated Sep. 27, 2016, for corresponding European Patent Application No. 14775414.

* cited by examiner

*Primary Examiner* — Robert S Landsman
*Assistant Examiner* — Bruce D Hissong
(74) *Attorney, Agent, or Firm* — Pergament & Cepeda LLP; Milagros A. Cepeda; Edward D. Pergament

(57) ABSTRACT

Provided is a method of refolding of recombinant GCSF that minimizes the generation of oxidized forms of GCSF by optimizing the refolding of inclusion bodies containing recombinant GCSF.

3 Claims, 1 Drawing Sheet

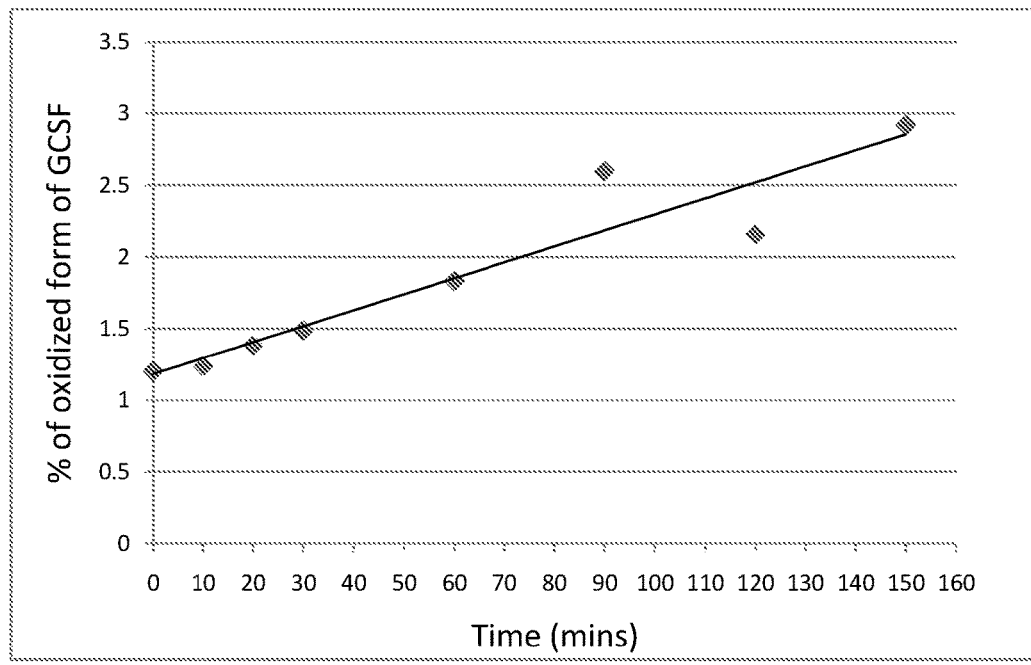

(12) United States Patent

REFOLDING OF GRANULOCYTE COLONY STIMULATING FACTOR

RELATED APPLICATION

This application is a National Stage Application under 35 U.S.C. § 371 of PCT International Application No. PCT/IB2014/060251, filed Mar. 28, 2014, which claims the benefit of Indian Provisional Application 1431/CHE/2013, filed 29 Mar. 2013, all of which are hereby incorporated by reference in their entireties.

FIELD OF THE INVENTION

The present invention relates to a refolding process for Granulocyte Colony Stimulating Factor (GCSF) from inclusion bodies.

BACKGROUND OF THE INVENTION

Differentiation and proliferation of hemtopoietic cells are regulated by glycoproteins referred to as colony stimulating factors (CSFs). Of the various CSFs, the Granulocyte Colony Stimulating Factor (GCSF) stimulates the proliferation of specific bone marrow precursor cells and their differentiation into granulocytes. When administered to mammals, GCSF promotes a dramatic increase in circulating granulocyte populations.

GCSF is one of several proteins produced by recombinant DNA technology for therapeutic use. Of the two types of GCSF clinically available, lenograstim, the glycosylated form of GCSF, is expressed in mammalian cells, and filgrastim, the non-glycosylated form is expressed in *Escherichia coli* (*E. coli*).

Proteins expressed by recombinant DNA methods in bacteria such as *E. coli*, are usually expressed as insoluble aggregates called inclusion bodies. These protein aggregates are separated, solubilized in the presence of denaturing agents. Solubilized protein is then refolded in presence of oxidizing agents. The refolded protein can then be further purified by appropriate column chromatographic procedures.

A typical production process for GCSF is described in U.S. Pat. No. 5,849,883. Recombinant GCSF is obtained by lysing *E. coli* cells and separating out the inclusion bodies containing GCSF. Inclusion bodies are then solubilized with deoxycholate and the extracted GCSF is refolded in the presence of a denaturant agent and an oxidizing agent. Refolded protein is further purified using two ion exchange chromatography steps.

In addition to U.S. Pat. No. 5,849,883, other prior art also disclose various methods for refolding of proteins. EP0547102 explains a process of solubilization of proteins by addition of cationic surfactant and providing conditions to allow for refolding.

EP1630173 teaches a method for solubilization of GCSF from inclusion bodies by using reduced glutathione and a denaturing agent for solubilizing inclusion bodies.

U.S. Pat. No. 7,538,198 and EP1434789 provide a process of refolding of a protein by subjecting a protein aggregate and a denaturing agent to increased pressure and removing the dissolved protein from the increased pressure to fold the protein.

US2011294990 explains a process of refolding a protein by using two chaotropic agents and US2011034678 describes a process of refolding of a protein by using guanidine in the refolding buffer.

WO2011113601 teaches a process for refolding of GCSF by using oxidized glutathione and at least one reversed phase chromatography.

GCSF, obtained by solubilization and refolding of inclusion bodies, contains the native, oxidized and the reduced forms of GCSF. The reduced forms of GCSF are reported to form aggregates, whereas the oxidized form of GCSF have reduced bioactivity (Reubsaet et al., J. Pharm. Biomed. Anal. 17, 283-289, 1998). Generally, a chromatographic step is used downstream of refolding which caters to removal of the oxidized impurities generated during solubilization and refolding.

Refolding of GCSF by methods as discussed in the above stated prior art, results in higher presence of oxidized impurities resulting in sub-optimal yields of the correctly folded biologically active protein. Methods to reduce the creation of these oxidized impurities during solubilization would circumvent the need for an additional step to remove oxidized impurities. The current invention provides a method to reduce the generation of oxidized impurities by an optimized solubilization process during refolding of GCSF.

SUMMARY OF THE INVENTION

The present invention discloses a method for refolding of recombinant GCSF that minimizes the generation of oxidized forms of GCSF by optimizing the solubilization of inclusion bodies containing recombinant GCSF. The invention discloses a method for optimal time for solubilization of inclusion bodies during the refolding process to improve the yield of correctly folded form of GCSF with significant reduction in oxidized forms generated during the process.

BRIEF DESCRIPTION OF THE DRAWINGS

FIG. 1: Effect of incubation time on solubilized inclusion bodies (at pH 12) prior to adding refolding buffer. Oxidized forms of GCSF (out-put parameter), is measured in refolded protein solution.

DETAILED DESCRIPTION OF THE INVENTION

Proteins expressed by recombinant DNA methods in prokaryotic systems such as *E. coli*, are usually expressed as insoluble aggregates called inclusion bodies which require denaturation and renaturation (refolding) in order to recover the correctly folded biologically active form. The term "inclusion bodies" refer to the insoluble aggregates of proteins expressed by recombinant DNA methods in microbial expression systems.

The term "Oxidized forms of GCSF" as used herein refers to methionine oxidation(s) at 1 or more site(s) in the GCSF molecule The term "refolding buffer" as used herein refers to a buffer that is used in renaturation or refolding of the protein of interest.

The present invention provides a method for refolding GCSF obtained from inclusion bodies, wherein oxidized form of GCSF is reduced to less than 2%.

In an embodiment, the invention provides a method of refolding GCSF obtained from inclusion bodies by solubilization at about pH 11 to 12 wherein there is no incubation after the solubilization step and wherein the oxidized form of GCSF is reduced to less than 2%.

In an embodiment, the invention provides a method of refolding GCSF obtained from inclusion bodies by a) solubilization at about pH 11 to about pH 12 wherein there is no incubation after the solubilization step.
b) adding a refolding buffer at about pH 8 to about pH 9.
c) addition of cystine/cysteine at about pH 9 and incubation for about 16 hrs.
wherein the oxidized forms of GCSF are reduced to less than 2%.

In an embodiment, the invention provides a method of refolding GCSF obtained from inclusion bodies by solubilization at about pH 11 to 12 wherein there is no incubation after the solubilization step and prior to adding the refolding buffer wherein the oxidized form of GCSF is reduced to less than 2%.

The invention is more fully understood by reference to the following examples. These examples should not, however, be construed as limiting the scope of the invention.

EXAMPLE 1

Isolation of Inclusion Bodies

Cells containing recombinant GCSF in the form of inclusion bodies are resuspended in phosphate buffered saline (PBS buffer) in the ratio of 5 mL PBS buffer per gram of cell pellet. The cell suspension in PBS buffer is stirred on a magnetic stirrer for 20 min to make a homogenous solution. The cell suspension is centrifuged at a relative centrifugal force (RCF) of 13000 for 30 min at a temperature of 4° C. After centrifugation, supernatant is discarded and the pellet is resuspended in lysis buffer (50 mM Tris and 10 mM EDTA) in the ratio of 10 ml lysis buffer per gram of pellet. The cell suspension in lysis buffer is stirred gently on a magnetic stirrer for 20 min.

The cell suspension is passed through the homogenizer two times at a pressure of 900-1000 bar till a drop in $OD_{600}$ equivalent to 70% is achieved. The cell lysate is collected and centrifuged at 13000 RCF for 30 min at 4° C. The pellet obtained is of the inclusion bodies.

EXAMPLE 2

Solubilization of Inclusion Bodies

Inclusion bodies obtained from example 1, are solubilized with 8 M urea and water for injection (WFI). The pH of this suspension is adjusted to 11 to 13 by adding small quantities of 1 N sodium hydroxide solution.

EXAMPLE 3

Refolding of Solubilized Protein

Without incubation, the solubilization mixture from example 2 is diluted 20 times by directly adding the refolding buffer (25 mM Tris, 1 mM EDTA and 0.6 M Arginine and 5% Sorbitol). The pH is adjusted to 8.6-9.4 by Glacial Acetic Acid at pH 9.0.

EXAMPLE 4

Redox Shuffling

After a 10 minute interval, the refolding mixture from example 3 is subject to redox shuffling by addition of 0.2 mM cysteine, after a 10 minute interval 1.8 mM cystine is added which is again followed by a 10 minute interval after which 0.2 mM cysteine is added. This mixture is incubated at 2-8° C. for 16 hours to obtain refolded GCSF.

We claim:
1. A method of refolding Granulocyte Colony Stimulating Factor (GCSF) obtained from inclusion bodies comprising the steps of;
   a) solubilization of inclusion bodies in denaturant at about pH 11 to about pH 12, wherein there is no incubation after the addition of denaturant;
   b) addition of a refolding buffer at about pH 8 to about pH 9 to the solubilized mixture of step (a);
   c) addition of redox shuffling mixture at about pH 9 to the refolded mixture of step (b) and incubation for about 16 hours;
      wherein the said method reduces the oxidized forms of GCSF to less than 1.5%.
2. The method according to claim 1, wherein the refolding buffer comprises a basic amino acid and a polyalcohol.
3. The method according to claim 1, wherein the redox shuffling mixture comprises about 0.2 mM cysteine and about 1.8 mM cystine.

* * * * *